United States Patent [19]

Lutz

[11] Patent Number: 5,250,718
[45] Date of Patent: * Oct. 5, 1993

[54] PROCESS FOR THE PREPARATION OF SECONDARY ALKYL SULFATE-CONTAINING SURFACTANT COMPOSITIONS

[75] Inventor: Eugene F. Lutz, Houston, Tex.

[73] Assignee: Shell Oil Company, Houston, Tex.

[*] Notice: The portion of the term of this patent subsequent to Dec. 24, 2008 has been disclaimed.

[21] Appl. No.: 951,955

[22] Filed: Sep. 28, 1992

[51] Int. Cl.$^5$ .............................................. C07C 315/04
[52] U.S. Cl. ........................................ 558/41; 558/42
[58] Field of Search ..................................... 558/41, 42

[56] References Cited

U.S. PATENT DOCUMENTS

| | | |
|---|---|---|
| 2,094,546 | 9/1937 | Lyons . |
| 2,640,070 | 5/1953 | Dahmen . |
| 2,945,818 | 7/1960 | Costine et al. . |
| 3,234,258 | 2/1966 | Morris . |
| 3,676,523 | 7/1972 | Mason . |
| 3,681,424 | 8/1972 | Bloch et al. . |
| 3,686,351 | 8/1972 | Mason . |
| 3,737,475 | 6/1973 | Mason . |
| 3,825,615 | 7/1974 | Lutz . |
| 3,893,940 | 7/1975 | Ohogoshi et al. . |
| 4,020,121 | 4/1977 | Kister et al. . |
| 4,052,342 | 10/1977 | Fernley et al. . |
| 4,088,598 | 5/1978 | Williams . |
| 4,226,797 | 10/1980 | Bakker et al. . |
| 4,474,678 | 10/1984 | Lutz et al. . |
| 4,544,493 | 10/1985 | Silvis . |
| 4,857,213 | 8/1989 | Caswell et al. . |
| 5,075,041 | 12/1991 | Lutz . |

FOREIGN PATENT DOCUMENTS

| | | |
|---|---|---|
| 884656 | 12/1961 | United Kingdom . |
| 1194862 | 6/1970 | United Kingdom . |
| 1585030 | 5/1978 | United Kingdom . |

OTHER PUBLICATIONS

Asinger, "The Hydration of Olefins to Alcohols," Mono-olefins: Chemistry and Technology, 1968, pp. 689–704.

Primary Examiner—Marianne M. Cintins
Assistant Examiner—John Peabody
Attorney, Agent, or Firm—Pamela J. McCollough

[57] ABSTRACT

This invention relates to a process for preparing secondary alkyl sulfate-containing surface active compositions substantially free of unreacted organic matter and water, which process comprises: a) sulfating a reactant selected from the group consisting of a detergent range olefin having from about 8 to about 22 carbon atoms, a detergent range alcohol having from about 8 to about 22 carbon atoms and mixtures thereof, with a sulfating agent, b) neutralizing the product of step a) with a base dispersed in a non-surfactant carrier, c) saponifying the product of step b), d) passing the product of step c) through a thin film evaporator to evaporate unreacted organic matter from said product and recovering a secondary alkyl sulfate-containing product.

34 Claims, No Drawings

PROCESS FOR THE PREPARATION OF SECONDARY ALKYL SULFATE-CONTAINING SURFACTANT COMPOSITIONS

FIELD OF THE INVENTION

This invention relates to a process for the preparation of secondary alkyl sulfate-containing surfactant compositions.

BACKGROUND OF THE INVENTION

This invention provides a process for preparing surfactant compositions comprising secondary alkyl sulfates which are substantially free of unreacted organic matter (UOM), and which are substantially free of water, thus making the compositions substantially free of inert diluents.

In conventional practice, secondary alkyl sulfates have been prepared by reaction of olefins or alcohols with sulfuric acid, followed by neutralization of the intermediate secondary alkyl sulfuric acid with aqueous base, usually sodium hydroxide. The process for preparing secondary alkyl sulfates is complicated by incomplete reaction of the starting olefin or alcohol and by formation of dialkyl sulfates which saponify during the neutralization step, noted above, to equal molar amounts of secondary alkyl sulfate and secondary alcohol.

Unreacted olefin and secondary alcohol, which can amount to 50% by weight or more of the starting olefin, are generally removed from the secondary alkyl sulfate by a process of extraction with an organic solvent as described in U.S. Pat. No. 4,175,092. The extraction process can be complicated by the formation of undesirable emulsions and gels as well as by the dissolution of some of the extracting solvent in the aqueous secondary alkyl sulfate phase. Extracting solvents frequently have objectionable odors and must be removed from the aqueous surfactant solution, an operation which can be accompanied by severe foaming difficulties. When extraction is complete, the concentration of secondary alkyl sulfate in water is generally in the range of 20-40% by weight (F. Asinger, *Mono-Olefins: Chemistry and Technology*, 1968, pp. 689-694).

It would therefore be advantageous to have a process for preparing surfactant compositions utilizing secondary alkyl sulfates as the anionic component which eliminates the problems associated with solvent extraction for removal of the non-surface active organic material and which produces a product free of water, thus allowing maximum handling and blending flexibility.

An integrated process for preparing surfactant compositions has been found in which secondary alkyl sulfates derived from olefins and/or alcohols can be generated in a manner such that the non-surface active material can be easily stripped from the secondary alkyl sulfates while at the same time producing a surfactant and/or detergent composition which is particularly useful for household applications.

It is therefore an object of this invention to prepare surface active compositions containing secondary alkyl sulfates derived from olefins and/or alcohols, which are substantially free of unreacted olefin and substantially free of water, in a non-surfactant carrier. In the present invention, a surface active composition is prepared by reacting a detergent range alcohol and/or a detergent range olefin with a sulfating agent, removing excess sulfating agent, neutralizing and saponifying the mixture in the presence of a base dispersed in a non-surfactant carrier, and then passing the mixture through a falling film or wiped film evaporator to strip unreacted organic matter from the mixture, thereby producing a secondary alkyl sulfate-containing detergent composition which is anhydrous and substantially free of inert diluents.

SUMMARY OF THE INVENTION

This invention relates to a process for preparing secondary alkyl sulfate-containing surface active compositions substantially free of unreacted organic matter and water, which process comprises: a) sulfating a reactant selected from the group consisting of a detergent range alcohol having from about 8 to about 22 carbon atoms, a detergent range olefin having from about 8 to about 22 carbon atoms and mixtures thereof, with a sulfating agent, and, optionally, removing excess sulfating agent by water wash, b) neutralizing the product of step a) with a base dispersed in a non-surfactant carrier, c) saponifying the product of step b), d) passing the product of step c) through a thin film evaporator to evaporate unreacted organic matter from said product and recovering said product. The unreacted organic matter evaporated from the product can be recycled, if desired.

DESCRIPTION OF THE PREFERRED EMBODIMENTS

This invention relates to secondary alkyl sulfate-containing surface active compositions substantially free of unreacted organic matter and water prepared by a process which comprises sulfation of a detergent range alcohol and/or a detergent range olefin by adding a sulfating agent followed by water washing to remove excess sulfuric acid, neutralization with a base dispersed in a non-surfactant carrier, and then distillation of unreacted organic matter, thus generating a surfactant composition comprising secondary alkyl sulfate and a non-surfactant carrier.

As used herein, the phrase "substantially free of unreacted organic matter and water" refers to detergent compositions which contain less than about 10 percent by weight, preferably less than about 5 percent by weight, of unreacted organic matter and less than about 5 percent by weight, preferably less than about 2 percent by weight, of water.

The detergent range olefins which are suitable for use in the present invention are olefins containing from about 8 to about 22 carbon atoms. These olefins can be alpha olefins or internal olefins and they may be linear or branched, but are preferably linear or lightly branched. Single cut olefins or mixtures of olefins may also be used. In a particularly preferred embodiment, the olefin contains from about 12 to about 18 carbon atoms.

Preferred for use as olefin reactant for the practical reason of availability are the commercial olefin products in the $C_8$ to $C_{22}$ range. While commercial production of such olefins may be carried out by the cracking of paraffin wax, commercial production is more commonly accomplished by the oligomerization of ethylene using procedures well known in the art. The resulting oligomerization products are substantially of linear structure and thus products are substantially of linear structure. Commercial olefin products manufactured by ethylene oligomerization are marketed in the United States by Shell Chemical Company under the trademark Neodene and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121, the teachings of which are incorporated herein by reference. While most of such olefin products are comprised largely of alpha-olefins, higher linear internal olefins are also commercially produced, for example, by the chlorinationdehydrochlorination of paraffins, by paraffin dehydrogenation, and by isomerization of alpha-olefins. Linear internal olefin products in the $C_8$ to $C_{22}$ range are marketed by Shell Chemical Company and by Liquichemica Company. These commercial products, whether predominantly internal or alpha-olefins typically contain about 70 percent by weight or more, most often about 80 percent by weight or more, linear mono-olefins in a specified carbon number range (e.g., $C_{10}$ to $C_{12}$, $C_{11}$ to $C_{15}$, $C_{12}$ to $C_{13}$, $C_{15}$ to $C_{18}$, etc.), the remainder of the product being olefin of other carbon number or carbon structure, diolefins, paraffins, aromatics, and other impurities resulting from the synthesis process. Olefins marketed in the United States in the $C_{12}$ to $C_{18}$ range are considered most preferred for use in the instant invention.

The detergent range alcohols which are suitable for use in the present invention are alcohols containing from about 8 to about 22 carbon atoms. Acyclic aliphatic alcohols having from about 9 to about 18 carbon atoms form a preferred class of reactants, particularly the secondary alcohols, although primary alcohols can also be utilized. As a general rule, the carbon chains of the alcohols may be of either branched or linear (straight-chain) structure, although alcohol reactants in which greater than about 50 percent, more preferably greater than about 70 percent and most preferably greater than about 90 percent of the molecules are of linear (straight-chain) carbon structure are preferred. In large part, such preferences relate more to the utility and value of the products than to the operability or performance of the process of the invention.

Specific examples of branched chain or secondary alcohols include secondary tetradecanols, secondary hexadecanols, 2-tetradecanol, 2-hexadecanol and the like. Commercially available mixtures of secondary alcohols prepared via the oxidation of paraffins, and from internal olefins and alphaolefins mixtures via sulfation and hydrolysis reactions are also suitable. Specific examples of commercially available secondary alcohol mixtures include Tergitol 15, a trademark of and sold by Union Carbide, in which the main components are $C_{11}$ to $C_{15}$ compounds; Tergitol 45, in which the main components are $C_{14}$ to $C_{15}$ compounds; Softanol 24, a trademark of and sold by Nippon Shokubai Kagaku Kogyo Co., Ltd., in which the main components are $C_{12}$ to $C_{14}$ compounds, and the like.

Specific examples of suitable primary straight-chain monohydric aliphatic alcohols include dodecanol, pentadecanol, octadecanol, eicosanol and the like. Mixtures of alcohols are also suitable for purposes of the invention and are often preferred for reasons of commercial availability. Commercially available mixtures of primary monoalcohols prepared via the oligomerization of ethylene and the hydroformylation or oxidation and hydrolysis of the resulting higher olefins are particularly preferred. Specific examples of commercially available alcohol mixtures in the $C_9$ to $C_{20}$ range include the NEODOL Alcohols, trademark of and sold by Shell Chemical Company, including mixtures of $C_9$, $C_{10}$ and $C_{11}$ alcohols (NEODOL 91 Alcohol), mixtures of $C_{12}$ and $C_{13}$ alcohols (NEODOL 23 Alcohol), mixtures of $C_{12}$, $C_{13}$, $C_{14}$, and $C_{15}$ alcohols (NEODOL 25 Alcohol), and mixtures of $C_{14}$ and $C_{15}$ alcohols (NEODOL 45 Alcohol); the ALFOL Alcohols, trademark of and sold by Vista Chemical Company, including mixtures of $C_{10}$ and $C_{12}$ alcohols (ALFOL 1012), mixtures of $C_{12}$ and $C_{14}$ alcohols (ALFOL 1214), mixtures of $C_{16}$ and $C_{18}$ alcohols (ALFOL 1618), and mixtures of $C_{16}$, $C_{18}$ and $C_{20}$ alcohols (ALFOL 1620); the EPAL Alcohols, trademark of and sold by Ethyl Chemical Company, including mixtures of $C_{10}$ and $C_{12}$ alcohols (EPAL 1012), mixtures of $C_{12}$ and $C_{14}$ alcohols (EPAL 1214), and mixtures of $C_{14}$, $C_{16}$, and $C_{18}$ alcohols (EPAL 1418); and the TERGITOL-L Alcohols, trademark of and sold by Union Carbide Corporation, including mixtures of $C_{12}$, $C_{13}$, $C_{14}$, and $C_{15}$ alcohols (TERGITOL-L 125). Also very suitable are the commercially available alcohols prepared by the reduction of naturally occurring fatty esters, for example, the CO and TA products of Procter and Gamble Company and the TA alcohols of Ashland Oil Company.

As used herein, the term "alcohol reactant" is also intended to include ethoxylated alcohols or alcohol ethoxylates. The general class of alcohol ethoxylates useful in the present invention is characterized by the chemical formula $R_1-O-(CH_2-CH_2O)_n-H$, wherein $R_1$ is a straight-chain or branched-chain alkyl group having in the range of from about 8 to about 22 carbon atoms, preferably from about 12 to about 18 carbon atoms, or an alkylaryl group having an alkyl moiety having from about 8 to about 12 carbon atoms, and n represents the average number of oxyethylene groups per molecule and is in the range of from about 0.5 to about 15, preferably from about 2 to about 12 and more preferably from about 2 to about 9. The alkyl group can have a carbon chain which is straight or branched, and the ethoxylate component can be a combination of straight-chain and branched molecules. Preferably, about 75 percent of the R groups in the instant composition are straight-chain. It is understood that R can be substituted with any substituent which is inert. Ethoxylates within this class are conventionally prepared by the sequential addition of ethylene oxide to the corresponding alcohol (ROH) in the presence of a catalyst.

The alcohol ethoxylate is preferably derived by ethoxylation of primary or secondary, straight-chain or branched alcohols. Suitably, the alcohols have from about 8 to about 18 carbon atoms, preferably from about 9 to about 15 carbon atoms, and more preferably from about 12 to about 15 carbon atoms. The most common ethoxylates in this class and the ones which are particularly useful in this invention are the primary alcohol ethoxylates, i.e., compounds of formula I in which R is an alkyl group and the $-O-(CH_2-CH_2O)_n-H$ ether substituent is bound to a primary carbon of the alkyl group.

Specific ethoxylated alcohols which can be used in the present invention include ethoxylated fatty alcohols, preferably linear primary or secondary monohydric alcohols with about $C_8$ to about $C_{22}$, preferably about $C_{12}$ to about $C_{15}$, alkyl groups and an average of about 0.5 to about 15, preferably about 2 to about 9, moles of ethylene oxide per mole of alcohol, and ethoxylated alkylphenols with $C_8$ to about $C_{12}$ alkyl groups, preferably about $C_8$ to about $C_{10}$ alkyl groups and an average of about 1 to about 12 moles of ethylene oxide per mole of alkylphenol.

In a preferred embodiment, the alcohol reactant is a primary alcohol, preferably selected from the group consisting of dodecanol, tridecanol, tetradecanol, pentadecanol and mixtures thereof.

In the process of the present invention, it is particularly preferred to use a detergent range olefin reactant or alternatively, a reactant which is a mixture of a detergent range olefin and a detergent range alcohol. For example, a $C_{14/18}$ internal olefin of the following composition: $C_{14}$, 3.5 percent by weight(% w); $C_{15}$, 41.8% w; $C_{16}$, 36.5% w; $C_{17}$, 15.3% w, and $C_{18}$, 3.0% w; admixed with the corresponding secondary alcohols is a particularly suitable feedstock. When a detergent range olefin is used as reactant, an alpha olefin of carbon range $C_{14/18}$ or an internal olefin of the same carbon number range is a good feed. When a mixture of a detergent range olefin and a detergent range alcohol is used, $C_{14/18}$ alpha or internal olefin and $C_{14/18}$ secondary alcohols are particularly suitable as feed.

The sulfating agents suitable for use in sulfating the detergent range olefins and/or alcohols in step a) include those compounds capable of forming the carbon to oxygen to sulfur bonds necessary for the formation of an alkyl sulfate. The particular sulfating agents used are typically a function of the compounds to be sulfated. These sulfating agents are known in the art and include sulfuric acid salts for the sulfation of olefins, and sulfur trioxide, chlorosulfonic acid or oleum for the sulfation of alcohols. In a preferred embodiment, the reactants in step a) are detergent range olefins or a mixture of detergent range olefins and detergent range alcohols and the sulfating agent is concentrated sulfuric acid.

When concentrated sulfuric acid used to sulfate detergent range olefins or a mixture of detergent range olefins and detergent range alcohols, the concentrated sulfuric acid is typically from about 75 percent by weight to about 100 percent by weight, preferably from about 85 percent by weight to about 98 percent by weight, in water. Suitable amounts of sulfuric acid are generally in the range of from about 0.3 moles to about 1.3 moles of sulfuric acid per mole of olefin and/or alcohol, preferably from about 0.4 moles to about 1.0 mole of sulfuric acid per mole of olefin and/or alcohol.

The sulfation reaction in step a) is suitably carried out at temperatures in the range of from about $-20°$ C. to about 50° C., preferably from about 5° C. to about 40° C., and at pressures in the range of from about 1 atmosphere to about 5 atmospheres, preferably from about 1 atmosphere to about 2 atmospheres, and more preferably, about 1 atmosphere. Suitable residence times for the sulfation reaction range from a few minutes to several hours, preferably from about 2 minutes to about 10 hours and more preferably, from about 5 minutes to about 2 hours.

The sulfation reaction for a detergent range olefin reactant may be illustrated by the following equation:

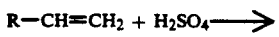

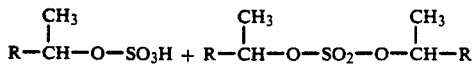

wherein R is an alkyl group having from about 6 to about 20 carbon atoms. The products of the sulfation reaction are primarily monoalkyl sulfuric acids and dialkyl sulfates along with unreacted olefin and unreacted sulfuric acid.

In one embodiment, the products of the sulfation reaction in step a) may, prior to neutralization, be subjected to deacidification for the partial or substantially complete removal of the unreacted sulfuric acid or any other unreacted sulfating agent. Suitable deacidification procedures include washing the sulfation reaction product with water or an acid such as sulfuric acid having a concentration of from about 75 percent by weight to about 90 percent by weight, preferably from about 80 percent by weight to about 85 percent by weight, in water. The deacidification is typically carried out at the same temperature at which the sulfation reaction in step a) is carried out. While the present invention may be carried out with or without deacidification, in a preferred embodiment, the product of the sulfation reaction in step a) is deacidified by washing with 82% w sulfuric acid to remove as much unreacted sulfuric acid as possible.

Following the sulfation reaction in step a) and optional deacidification, the sulfation product, i.e., monoalkyl and dialkyl sulfates, are contacted with a base dispersed in a non-surfactant carrier in order to neutralize the alkyl sulfuric acid portion of the sulfation product of step a) to form the corresponding sulfuric acid salts.

The neutralization reaction is accomplished using one or more bases such as ammonium or alkali metal or alkaline earth metal hydroxides or carbonates or bicarbonates dispersed in a non-surfactant carrier. Suitable bases include sodium hydroxide, sodium carbonate, potassium hydroxide, calcium hydroxide and the like, with sodium hydroxide or potassium hydroxide being the preferred base. The amount of base added to the non-surfactant carrier is based on the acidity of the monoalkylsulfuric acid phase after water washing and is suitably in the range of from about 1.1 meq/meq acid (milliequivalent per milliequivalent of acid) to about 2.5 meq/meq acid, preferably from about 1.3 meq/meq acid to about 1.9 meq/meq acid.

The neutralization procedure can be carried out over a wide range of temperatures and pressures. Typically, the neutralization procedure is carried out at a temperature in the range of from about 20° C. to about 65° C., and a pressure in the range of from about 1 atmosphere to about 2 atmospheres. The neutralization time is typically in the range of from about 0.5 hours to about 1.0 hours.

The non-surfactant carrier utilized in the neutralization reaction in step b) must be a liquid or at least be sufficiently flowable to pass through a thin film evaporator. Suitable non-surfactant carriers include alkyl glycols, polyether glycols, glycerine and mixtures thereof, with preference being given to alkyl glycols and/or polyether glycols.

In a preferred embodiment, the non-surfactant carrier is one or more alkyl glycols or polyether glycols of the formula

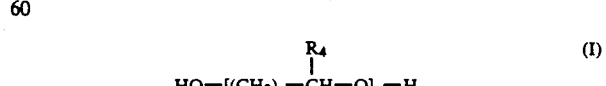

wherein x is an integer in the range of 1 to about 20, y is an integer in the range of 1 to about 3, and $R_4$ represents, individually in each occurrence, either hydrogen or alkyl, with the proviso that $R_4$ is hydrogen when y is 2 or 3. The glycol molecules may contain from 1 to about 10 ether groups, each of which may individually be ethoxy (—$CH_2$—$CH_2$—O—), propoxy (—$CH_2$—$CH_2$—$CH_2$—O—), or isopropoxy (—$CH_2$—$CH(CH_3)$—O—). The glycols may also, for convenience, be referred to as selected from the class consisting of $C_2$ and $C_3$ alkyl glycols, i.e., ethylene glycol, 1,2-propanediol, 1,3-propanediol, 1,4-butanediol and also consisting of polyether glycol condensation products of between 2 and about 20 of said alkyl glycols. Particularly good results are obtained using glycols of formula I wherein $R_4$ is hydrogen or methyl. Preferably, the glycol molecules contain from 1 to about 10, more preferably from 1 to about 8, ether groups. From the standpoint of availability and cost of the glycols, those with from 1 to about 4 ether groups are still more preferred for use in the present invention.

Alkyl glycols and polyether glycols suitable for use as nonsurfactant carriers in the present invention are well known and commercially available materials. The lower glycols, e.g., ethylene glycol, diethylene glycol, tetraethylene glycol, propyleneglycol, and 1,4-butanediol, etc., are specifically available, while the higher polyether glycols are typically available as mixtures of compounds having a range of ether groups. Specific or relatively narrow range higher glycols can be obtained from such mixtures, if desired, by distillation.

In a particularly preferred embodiment, the non-surfactant carrier is an alkyl glycol or polyether glycol selected from the group consisting of 1,2-propanediol, diethylene glycol, ethylene glycol, 1,4-butanediol and mixtures thereof.

The amount of non-surfactant carrier in step b) in the present invention is such that it is sufficient to disperse in the desired base and such that the amount of non-surfactant carrier in the final surfactant composition is from about 30 percent by weight to about 90 percent by weight, preferably from about 35 percent by weight to about 60 percent by weight, and more preferably from about 30 percent by weight to about 50 percent by weight. Typically, the amount of non-surfactant carrier utilized in step b) is in the range of from about 30 percent by weight to about 90 percent by weight, and preferably from about 35 percent by weight to about 60 percent by weight, basis the weight of the final product.

The product may be de-salted following the neutralization reaction. A de-salting treatment may be used in place of or in addition to the de-acidification described above depending on the extent of the de-acidification. Desalting is typically carried out by using an excess of base in the neutralization reaction which neutralizes the unreacted sulfuric acid to form the inorganic salts thereof in addition to neutralizing the secondary alkyl sulfuric acids. For example, sodium sulfate may be present when sodium hydroxide is the base in the neutralization. These inorganic salts may be removed as a separate phase by known methods such as, for example, filtration. However, removal of the inorganic salts in this manner results in a loss of sulfuric acid, since the organic salts thereof are normally discarded. For this reason, removal of unreacted sulfuric acid by deacidification via water washing following sulfation is preferred.

Following the contact in step b) of the sulfation product of step a) with a base dispersed in a non-surfactant carrier to effect neutralization, the product of step b), is heated in step c) to a temperature in the range of from about 70° C. to about 115° C. in order to effect saponification or hydrolysis of the dialkyl sulfates to form equimolar amounts of alkyl sulfuric acid salts and secondary alcohols. Suitably, the neutralization and saponification reactions take place by the addition of one or more bases such as amines or ammonium or alkali metal or alkaline earth metal hydroxides, carbonates or bicarbonates dispersed in a non-surfactant carrier, with sodium hydroxide being the preferred base.

The saponification reaction can be carried out over a wide range of temperatures and pressures. The saponification procedure is typically carried out at a temperature in the range of from about 70° C. to about 115° C., preferably from about 80° C. to about 105° C., and a pressure of from about 1 atmosphere to about 2 atmospheres. The saponification reaction is generally carried out over a time period ranging from about 0.25 hours to about 5.0 hours.

The neutralization and saponification reactions may be illustrated by the following equations:

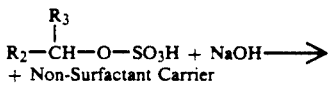

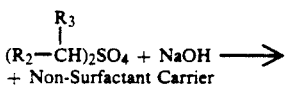

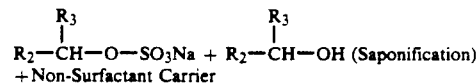

wherein $R_2$ and $R_3$ are alkyl groups having from about 1 to about 20 carbon atoms.

Following the neutralization and saponification reactions in steps b) and c), the product of step c) is passed through a thin film evaporator in order to remove unreacted olefin and secondary alcohols. The thin film evaporator may suitably be a wiped film evaporator or a falling film evaporator. If desired, the secondary alcohol can be separated from unreacted olefin by means recognized by those skilled in the art such as, for example, distillation.

After the product is passed through an evaporator to remove unreacted organic matter, the resulting secondary alkyl sulfate-containing product is recovered. The product contains primarily secondary alkyl sulfate and non-surfactant carrier, at least about 70 percent by weight to about 95 percent by weight, preferably about 85 percent by weight to about 95 percent by weight. The product generally contains from about 5 percent by weight to about 75 percent by weight, preferably from about 20 percent by weight to about 60 percent by weight secondary alkyl sulfate, and from about 20 percent by weight to about 80 percent weight, preferably from about 30 percent by weight to about 45 percent by weight non-surfactant carrier. Some residual level of sodium sulfate remains. The product typically contains less than about 12 percent by weight, preferably less than about 9 percent by weight, sodium sulfate.

Typically, the compositions of the invention have a surface active material content after thin film evaporation, i.e. the percentage of secondary alkyl sulfate plus the percentage of non-surfactant carrier, of at least about 70 percent by weight, preferably at least about 85 percent by weight, and more preferably, at least about 90 percent by weight of said composition. The compositions also contain from about 5 percent by weight to about 10 percent by weight sodium sulfate.

The surfactant compositions of the invention can be utilized in a variety of detergent applications. The surfactant compositions can be adsorbed at relatively low temperatures, about 85° C. or less, onto solid detergent materials such as, for example, sodium carbonate, in order to form dry detergent powders. The surfactant compositions can also be added to water or vice versa in order to form liquid detergents.

When 1,2-propanediol is used as the non-surfactant carrier in the instant process, the surfactant compositions prepared may suitably be a detergent formulation of the general sort as is conventionally made of ethoxylate-containing surfactant compositions. Commonly, but not necessarily, such a formulation would contain the surfactant composition of the instant invention in a quantity between about one and about fifty percent by weight. The remainder of such formulation would be comprised of one or more additional components which are conveniently used in ethoxylate-containing formulations, such as, for example, water; detergent builders; sequestering agents; coloring agents; enzymes; perfumes; and nonionic and anionic as well as cationic detergent active materials.

The ranges and limitations provided in the instant specification and claims are those which are believed to particularly point out and distinctly claim the present invention. It is, however, understood that other ranges and limitations which perform substantially the same function in substantially the same manner to obtain the same or substantially the same result are intended to be within the scope of the instant invention as defined by the instant specification and claims.

The invention will be described below by the following examples which are provided for purposes of illustration and are not to be construed as limiting the invention.

ILLUSTRATIVE EMBODIMENTS

EXAMPLE 1

Preparation of Surfactant Compositions

Sulfation

To a round-bottomed flask equipped with a paddle stirrer, thermometer, and addition funnel topped with a nitrogen blanket was added 150.00 grams of $C_{14}$ through $C_{18}$ internal olefin of the following composition: $C_{14}$, 3.5% w; $C_{15}$, 41.8% w; $C_{16}$, 36.5% w; $C_{17}$, 15.3% w, and $C_{18}$, 3.0% w. After cooling to 12° C., 73.94 grams of 95% sulfuric acid was added at such a rate that the temperature was maintained at 12°-21° C. When acid addition was complete, about 182 grams of the sulfation product was added to 161.35 grams of 82% sulfuric acid stirred for 15 minutes and then phase separated. The upper phase contained 176.75 grams and the lower phase contained 166.25 grams.

Neutralization/Saponification

The upper phase from the sulfation above (176.75 grams) was added to a stirred mixture of 180.00 grams of diethylene glycol and 44.96 grams of 50% sodium hydroxide, at 27°-54° C. over a period of nine minutes. The pH was 14 at the end of neutralization as measured with water wet pH paper.

After neutralization, the mixture was heated with stirring to reflux (approximately 102° C.) and held at reflux for more than two hours.

A sample after one hour at reflux gave an anionic concentration of 74.23 milliequivalents/100 grams. After two hours, the anionic concentration was 73.93 milliequivalents/100 grams. The alkalinity after saponification was complete was 0.171 milliequivalent/gram.

Thin Film Evaporation

To a wiped film evaporator at 140° C. and about 50 mm Hg pressure, was added 357.91 grams of the neutralized/saponified product from the above step. The wiped film evaporator distillation required eight minutes and produced 298.70 grams of bottoms product, which was redistilled at about 140° C. and about 19 mm Hg. The bottom product was redistilled 3 times through the wiped film evaporator at about 140° C. and at about 0.4–0.5 mm Hg pressure until the anionic content of the bottoms product was 185.72 milliequivalents/100 grams or 63.1% w.

EXAMPLE 2

Preparation of Surfactant Compositions

Sulfation

To a round-bottomed flask equipped with a paddle stirrer, thermometer, and addition funnel topped with a nitrogen blanket was added 150.00 grams of $C_{14}$ through $C_{18}$ internal olefin of the following composition: $C_{14}$, 3.5% w; $C_{15}$, 41.8% w; $C_{16}$, 36.5% w; $C_{17}$, 15.3% w, and $C_{18}$, 3.0% w. After cooling to 9° C., 74.19 grams of 95% sulfuric acid was added at such a rate that the temperature was maintained at 9°-21° C. When acid addition was complete, 161.36 grams of 82% sulfuric acid was added, stirred for 15 minutes, and then phase separated. The upper phase contained 195.66 grams and the lower phase contained 189.09 grams.

Neutralization/Saponification

The upper phase from the sulfation above (195.66 grams) was added to a stirred mixture of 180.00 grams of propylene glycol (non-surfactant carrier) and 42.39 grams of 50% sodium hydroxide, at 31°-51° C. over a period of eleven minutes. The pH was 14 at the end of neutralization as measured with water wet pH paper.

After neutralization, the mixture was heated with stirring to reflux (approximately 103°-105° C.) and held at reflux for more than two hours.

A sample after one hour at reflux gave an anionic concentration of 76.78 milliequivalents/100 grams. After two hours, the anionic concentration was 77.48 milliequivalents/100 grams. The alkalinity after saponification was complete was 0.043 milliequivalent/gram.

Thin Film Evaporation

To a wiped film evaporator at 111° C. and about 10 mm Hg pressure, was added 379.60 grams of the neutralized/saponified product from the above step. The wiped film evaporator distillation required eight minutes and produced 292.29 grams of bottoms product, which was redistilled at about 111° C. and about 5 mm Hg. The bottoms product was redistilled 3 times through the wiped film evaporator at about 111° C. and at about 0.4–0.5 mm Hg and 2 times at about 122° C. and about 0.3–0.35 mm Hg until the anionic content of the bottoms product was about 191.5 milliequivalents/100 grams or about 65% w.

What is claimed is:

1. A process for preparing secondary alkyl sulfate-containing surface active compositions substantially free of unreacted organic matter and water, which process comprises: a) sulfating a reactant selected from the group consisting of a detergent range olefin having from about 8 to about 22 carbon atoms, a detergent range alcohol having from about 8 to about 22 carbon atoms and mixtures thereof, with a sulfating agent, b) neutralizing the product of step a) with a base dispersed in a non-surfactant carrier, c) saponifying the product of step b), d) passing the product of step c) through a thin film evaporator to evaporate unreacted organic matter from said product and recovering a secondary alkyl sulfate-containing product.

2. The process of claim 1 wherein said reactant is a detergent range olefin having from about 12 to about 18 carbon atoms.

3. The process of claim 1 wherein said reactant is a mixture of a detergent range olefin having from about 12 to about 18 carbon atoms and detergent range alcohol having from about 12 to about 18 carbon atoms.

4. The process of claim 3 wherein said detergent range alcohol reactant is an ethoxylated alcohol having from about 12 to about 15 carbon atoms and from about 0.5 to about 9 moles of ethylene oxide per mole of alcohol.

5. The process of claim 1 wherein said sulfating agent is concentrated sulfuric acid having a concentration of from about 75 percent by weight to about 100 percent by weight in water.

6. The process of claim 1 wherein said sulfation step is carried out at a temperature in the range of from about 5° C. to about 40° C. and a pressure in the range of from about 1 atmosphere to about 2 atmospheres.

7. The process of claim 1 wherein following step a), the product of step a) is subjected to deacidification by water washing.

8. The process of claim 1 wherein said base in step b) is selected from amines or ammonium, alkali metal or alkaline earth metal hydroxides, carbonates or bicarbonates.

9. The process of claim 8 wherein said base is sodium hydroxide.

10. The process of claim 1 wherein said non-surfactant carrier in step b) is selected from the group consisting of alkyl glycols, polyether glycols, glycerine and mixtures thereof.

11. The process of claim 1 herein said non-surfactant carrier in step b) is an alkyl glycol.

12. The process of claim 11 wherein said alkyl glycol is selected from the group consisitng of 1,2-propanediol, diethylene glycol, ethylene glycol, 1,4-butanediol and mixtures thereof.

13. The process of claim 1 wherein said neutralization in step b) is carried out at temperatures in the range of from about 20° C. to about 65° C. and pressures in the range of from about 1 atmosphere to about 2 atmospheres.

14. The process of claim 1 wherein said saponification in step c) is carried out at a temperature in the range of from about 80° C. to about 105° C. and a pressure of from about 1 atmosphere to about 2 atmospheres.

15. The process of claim 1 wherein in step d), said thin film evaporator is a wiped film evaporator.

16. The process of claim 1 wherein said product recovered in step d) contains from about 5 percent by weight to about 75 percent by weight secondary alkyl sulfate and from about 20 percent by weight to about 90 percent by weight non-surfactant carrier.

17. The process of claim 16 wherein said product recovered in step d) contains from about 40 percent by weight to about 65 percent by weight secondary alkyl sulfate and from about 30 percent by weight to about 60 percent by weight non-surfactant carrier.

18. The process of claim 11 wherein said product recovered in step d) contains from about 5 percent by weight to about 75 percent by weight secondary alkyl sulfate and from about 20 percent by weight to about 90 percent by weight alkyl glycol.

19. The process of claim 18 wherein said product recovered in step d) contains from about 40 percent by weight to about 65 percent by weight secondary alkyl sulfate and from about 30 percent by weight to about 60 percent by weight alkyl glycol.

20. A process for preparing secondary alkyl sulfate-containing surface active compositions substantially free of unreacted organic matter and water, which process comprises: a) sulfating a reactant selected from the group consisting of a detergent range olefin having from about 8 to about 22 carbon atoms, a detergent range alcohol having from about 8 to about 22 carbon atoms, and mixtures thereof, with a sulfating agent, b) neutralizing the product of step a) with a base dispersed in an alkyl glycol having a formula

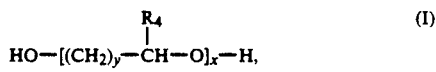

$$HO-[(CH_2)_y-CH(R_4)-O]_x-H, \quad (I)$$

wherein $R_4$ is hydrogen or an alkyl group having from about 1 to about 16 carbon atoms, x is an integer in the range of 1 to about 20, and y is an integer in the range of 1 to about 3, with the proviso that $R_4$ is hydrogen when y is 2 or 3, c) saponifying the product of step b), d) passing the product of step c) through a thin film evaporator to evaporate unreacted organic matter and recovering a secondary alkyl sulfate-containing product.

21. The process of claim 20 wherein said reactant is a detergent range olefin having from about 12 to about 18 carbon atoms.

22. The process of claim 20 wherein said reactant is a mixture of a detergent range olefin having from about 12 to about 18 carbon atoms and a detergent range alcohol having from about 12 to about 18 carbon atoms.

23. The process of claim 22 wherein said detergent range alcohol reactant is an ethoxylated alcohol having from about 12 to about 15 carbon atoms and from about 0.5 to about 9 moles of ethylene oxide per mole of alcohol.

24. The process of claim 20 wherein said sulfating agent is concentrated sulfuric acid having a concentration of from about 75 percent by weight to about 100 percent by weight in water.

25. The process of claim 20 wherein said sulfation in step a) is carried out at a temperature in the range of from about 5° C. to about 40° C. and a pressure in the range of from about 1 atmosphere to about 2 atmospheres.

26. The process of claim 20 wherein following step a), the product of step a) is subjected to deacidification by water washing.

27. The process of claim 20 wherein said base in step b) is selected from amines or ammonium, alkali metal or alkaline earth metal hydroxides, carbonates or bicarbonates.

28. The process of claim 27 wherein said base is sodium hydroxide.

29. The process of claim 20 wherein said neutralization in step b) is carried out at temperatures in the range of from about 20° C. to about 65° C. and pressures in the range of from about 1 atmosphere to about 2 atmospheres.

30. The process of claim 21 wherein said saponification in step c) is carried out at a temperature in the range of from about 80° C. to about 105° C. and a pressure of from about 1 atmosphere to about 2 atmosphere.

31. The process of claim 20 wherein in step d), said thin film evaporator is a wiped film evaporator.

32. The process of claim 20 wherein said product recovered in step d) contains from about 5 percent by weight to about 75 percent by weight secondary alkyl sulfate and from about 20 percent by weight to about 90 percent by weight alkyl glycol.

33. The process of claim 32 wherein said product recovered in step d) contains from about 40 percent by weight to about 65 percent by weight secondary alkyl sulfate and from about 30 percent by weight to about 60 percent by weight alkyl glycol.

34. The process of claim 20 wherein said composition contains at least about 85 percent by weight of secondary alkyl sulfate and non-surfactant carrier.

* * * * *